(12) United States Patent
Venisti

(10) Patent No.: US 9,272,064 B2
(45) Date of Patent: Mar. 1, 2016

(54) PERFUME DISPENSER FOR MOTOR VEHICLES

(71) Applicant: Millefiori S.r.l., Milan (IT)

(72) Inventor: Michele Venisti, Turin (IT)

(73) Assignee: Millefiori S.r.l., Milan (IT)

( * ) Notice: Subject to any disclaimer, the term of this patent is extended or adjusted under 35 U.S.C. 154(b) by 0 days.

(21) Appl. No.: 14/616,264

(22) Filed: Feb. 6, 2015

(65) Prior Publication Data
US 2015/0217017 A1    Aug. 6, 2015

(30) Foreign Application Priority Data

Feb. 6, 2014   (IT) .............................. TO2014A0024 U

(51) Int. Cl.
*A61L 9/12*    (2006.01)
*B60H 3/00*    (2006.01)

(52) U.S. Cl.
CPC ................ *A61L 9/12* (2013.01); *B60H 3/0028* (2013.01); *B60H 2003/0057* (2013.01)

(58) Field of Classification Search
CPC ........... A61L 9/015; A61L 9/12; A61L 9/122; A61L 9/125; A61L 9/127; B60H 3/0007; B60H 3/0014; B60H 3/0021; B60H 3/0028; B60H 2003/0057
USPC .................................................... 239/55–57
See application file for complete search history.

(56) References Cited

U.S. PATENT DOCUMENTS

| | | | | |
|---|---|---|---|---|
| 3,964,684 | A * | 6/1976 | Schimanski | A61L 9/12 239/56 |
| 4,194,690 | A * | 3/1980 | Stever | A01M 1/2055 239/57 |
| 6,161,820 | A * | 12/2000 | Wu | A61L 9/12 239/55 |
| 6,976,637 | B2 * | 12/2005 | Massimo | A61L 9/122 239/145 |
| 8,367,011 | B2 * | 2/2013 | Yamamoto | A01M 1/2033 239/53 |

(Continued)

FOREIGN PATENT DOCUMENTS

| | | |
|---|---|---|
| DE | 20207512 U1 | 8/2002 |
| WO | 2008/079351 A2 | 7/2008 |
| WO | 2008/079351 A3 | 7/2008 |

OTHER PUBLICATIONS

European Search report for corresponding European application No. 15154038.2, completed on Jun. 24, 2015, and dated Jul. 3, 2015.

*Primary Examiner* — Christopher Kim
(74) *Attorney, Agent, or Firm* — Heslin Rothenberg Farley & Mesiti P.C.; Victor A. Cardona, Esq.

(57) ABSTRACT

A perfume dispenser for motor vehicles includes a support bearing a perfume-dispensing body, wherein the support has a generally circular base provided with slits and an articulated dorsal attachment coupled to a supporting structure of a motor vehicle, and a front arm connected to the base and bent in front of this to form an open receptacle. The perfume-dispensing body consists of a flattened cylindrical casing set in a projecting way within the receptacle and connected in a coaxially rotatable way to the base. The casing contains a hydrophilic material soaked with a perfumed fluid and has dorsal slits facing the slits of the base of the support.

9 Claims, 5 Drawing Sheets

(56) References Cited

U.S. PATENT DOCUMENTS

| | | |
|---|---|---|
| 2004/0007787 A1 | 1/2004 | Kvietok et al. |
| 2008/0141928 A1* | 6/2008 | Adair ................ A01M 1/2033 116/206 |
| 2008/0210770 A1* | 9/2008 | Dever ................ A43D 3/1491 239/1 |
| 2008/0245890 A1* | 10/2008 | Lockwood .......... A01M 1/2055 239/60 |
| 2008/0257978 A1* | 10/2008 | Marth .................... A61L 9/048 239/60 |
| 2010/0314461 A1* | 12/2010 | Gruenbacher ............ A61L 9/12 239/6 |
| 2014/0314619 A1* | 10/2014 | Davanzo .................. A61L 2/18 422/4 |

\* cited by examiner

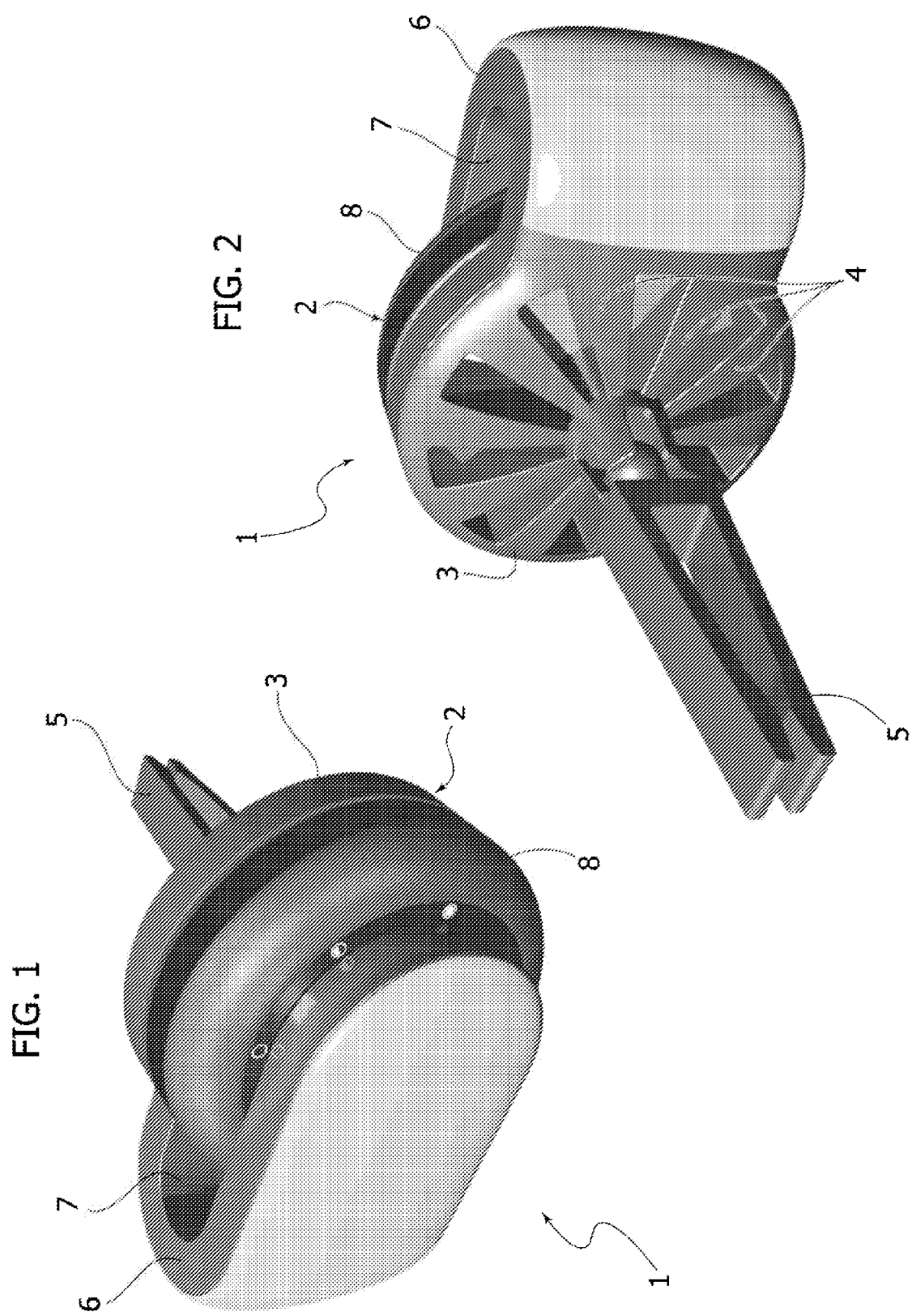

ND OF THE INVENTION

The object of the present invention is a perfume dispenser for motor vehicles, of the type comprising a support bearing a perfume-dispensing body, which presents a new and original shape designed to ensure a better functional effectiveness as compared to conventional perfume dispensers.

SUMMARY OF THE INVENTION

The perfume dispenser according to the invention is basically characterized in that the support comprises a generally circular base provided with slits and with an articulated dorsal attachment coupled to a supporting structure of the vehicle, and a front arm connected to the base and bent in front of this to form an open receptacle. The perfume-dispensing body consists of a flattened cylindrical casing set in a projecting way peripherally within the receptacle and connected in a coaxially rotatable way to the base. The casing contains a hydrophilic material soaked with a perfumed fluid and has dorsal slits facing the slits of the base of the support.

Thanks to this configuration, the perfume dispenser according to the invention, coupled to a supporting structure of the vehicle via the articulated dorsal attachment of the support, enables effective variation of the amount of the perfume dispensed by simply rotating the perfume-dispensing body with respect to the support so as to render the slits of the perfume-dispensing body and the slits of the base coinciding with one another to a graduatable extent, either more or less.

According to a preferred embodiment of the invention, the front arm is roughly shaped like a J, and the slits of the perfume-dispensing body and of the base are conveniently arranged like spokes, tapered from the periphery to the centre.

The hydrophilic material contained in the perfume-dispensing body is conveniently a constant-volume absorbent material.

BRIEF DESCRIPTION OF THE DRAWINGS

The invention will now be described in detail with reference to the annexed drawings, which are provided purely by way of non-limiting example and in which:

FIG. 1 is a front perspective view of a perfume dispenser for motor vehicles according to the invention;

FIG. 2 is a dorsal perspective view of the perfume dispenser;

DETAILED DESCRIPTION OF INVENTION

Figure 3:
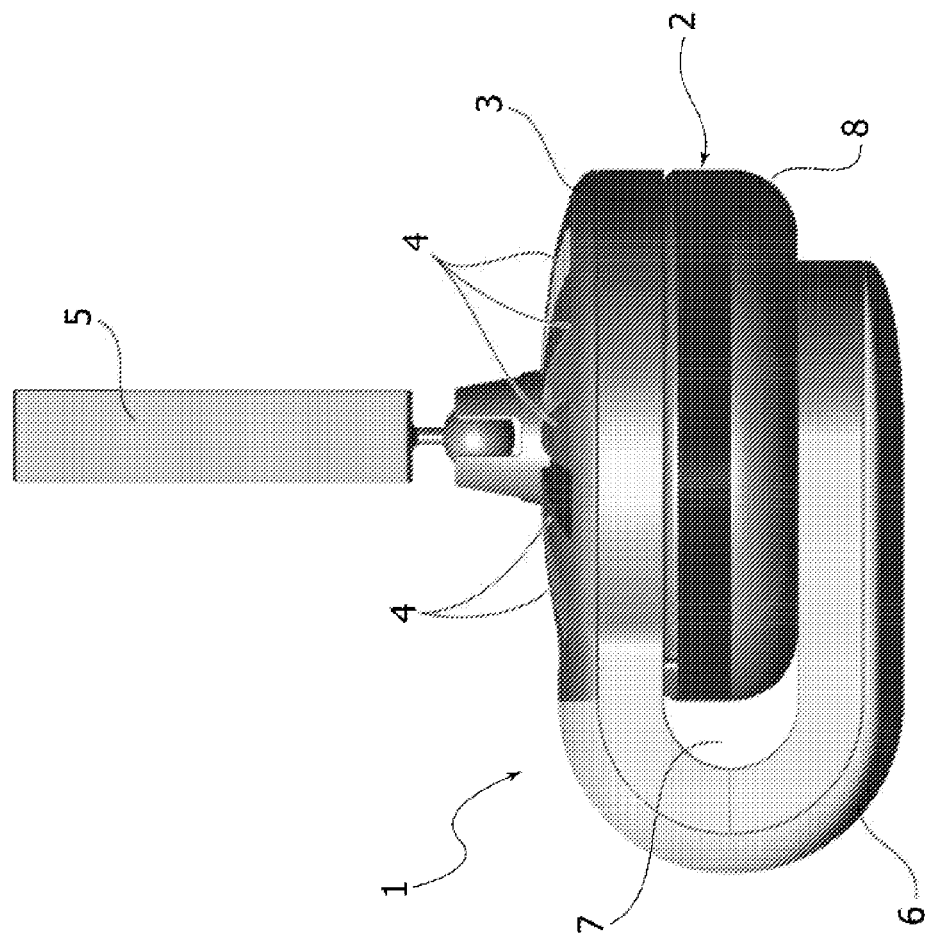
FIG. 3 is a top plan view of the perfume dispenser.
Figure 4:
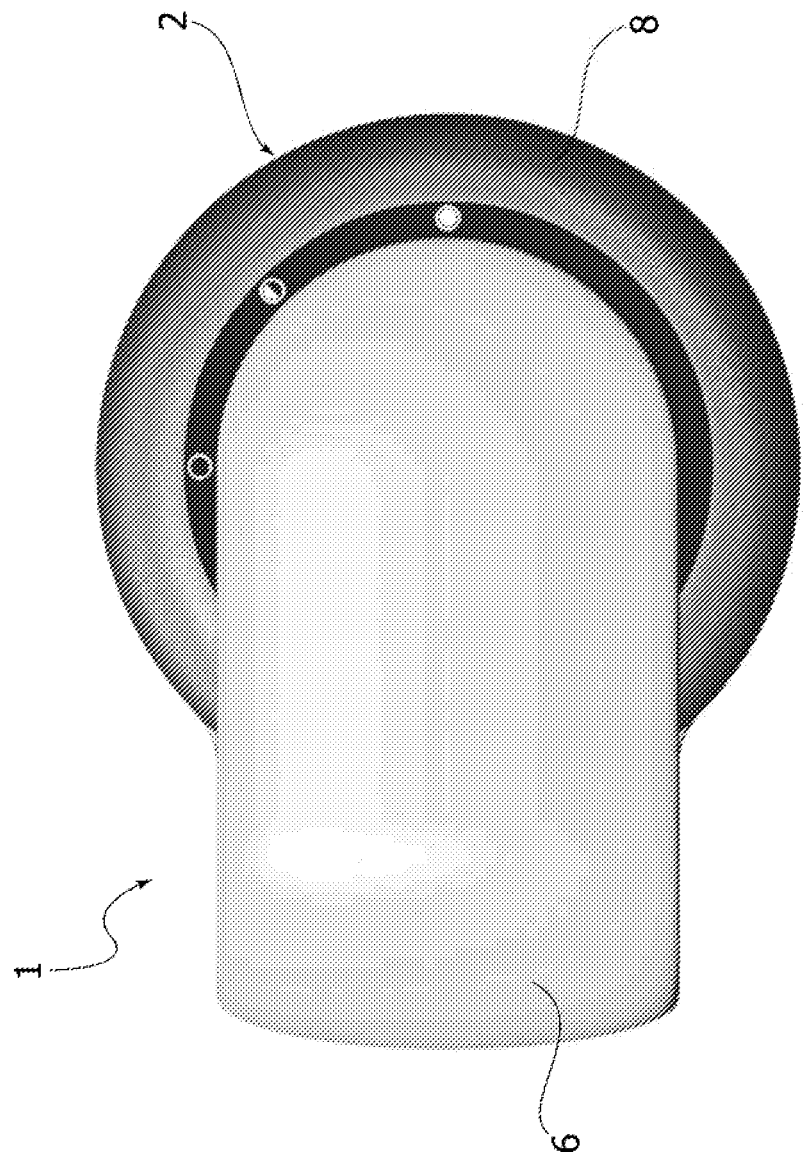
FIG. 4 is a front view of the perfume dispenser.
Figure 5:
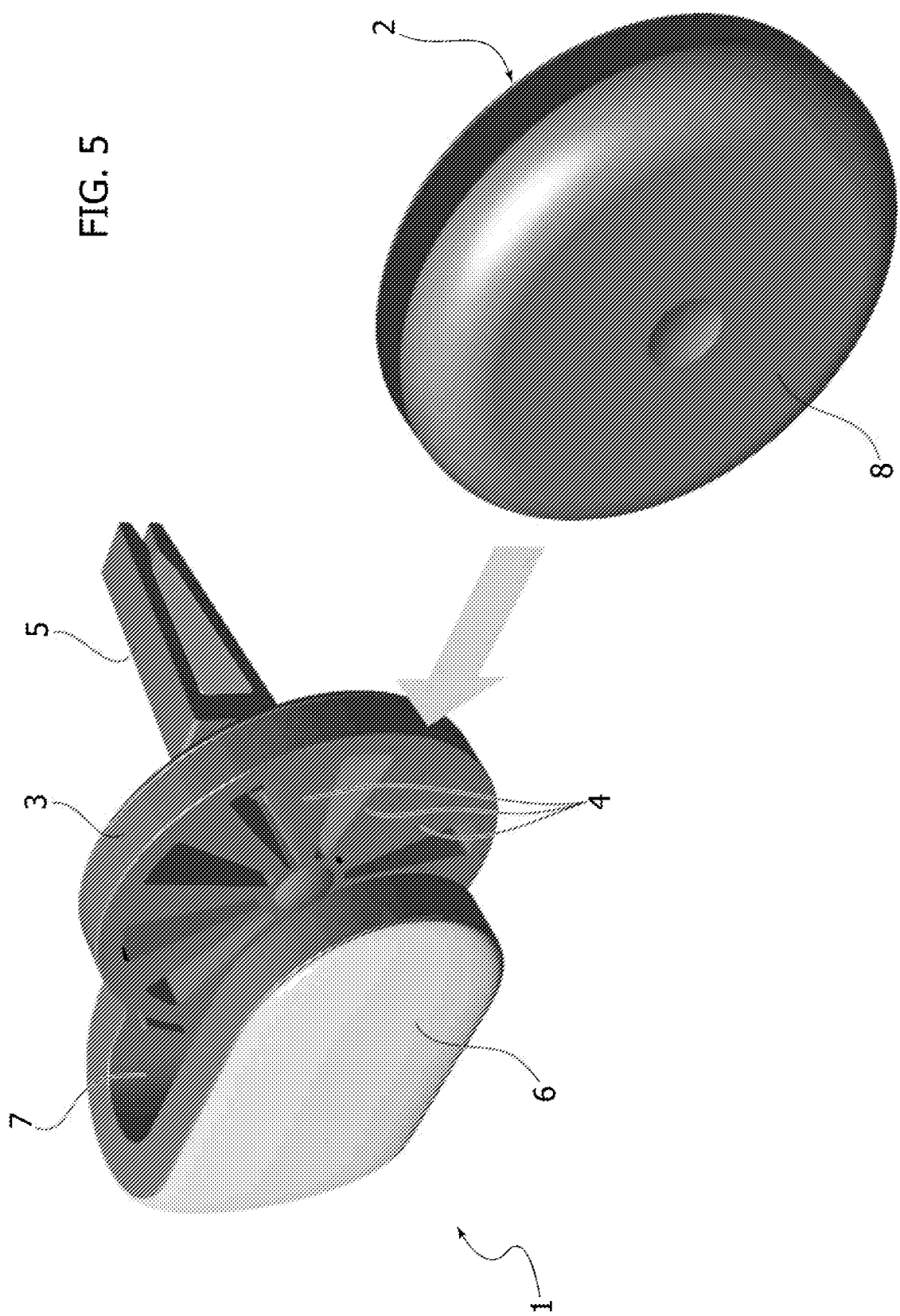
FIGS. 5 and 6 are two exploded perspective views, respectively a front view and a dorsal view, of the perfume dispenser.
Figure 6:
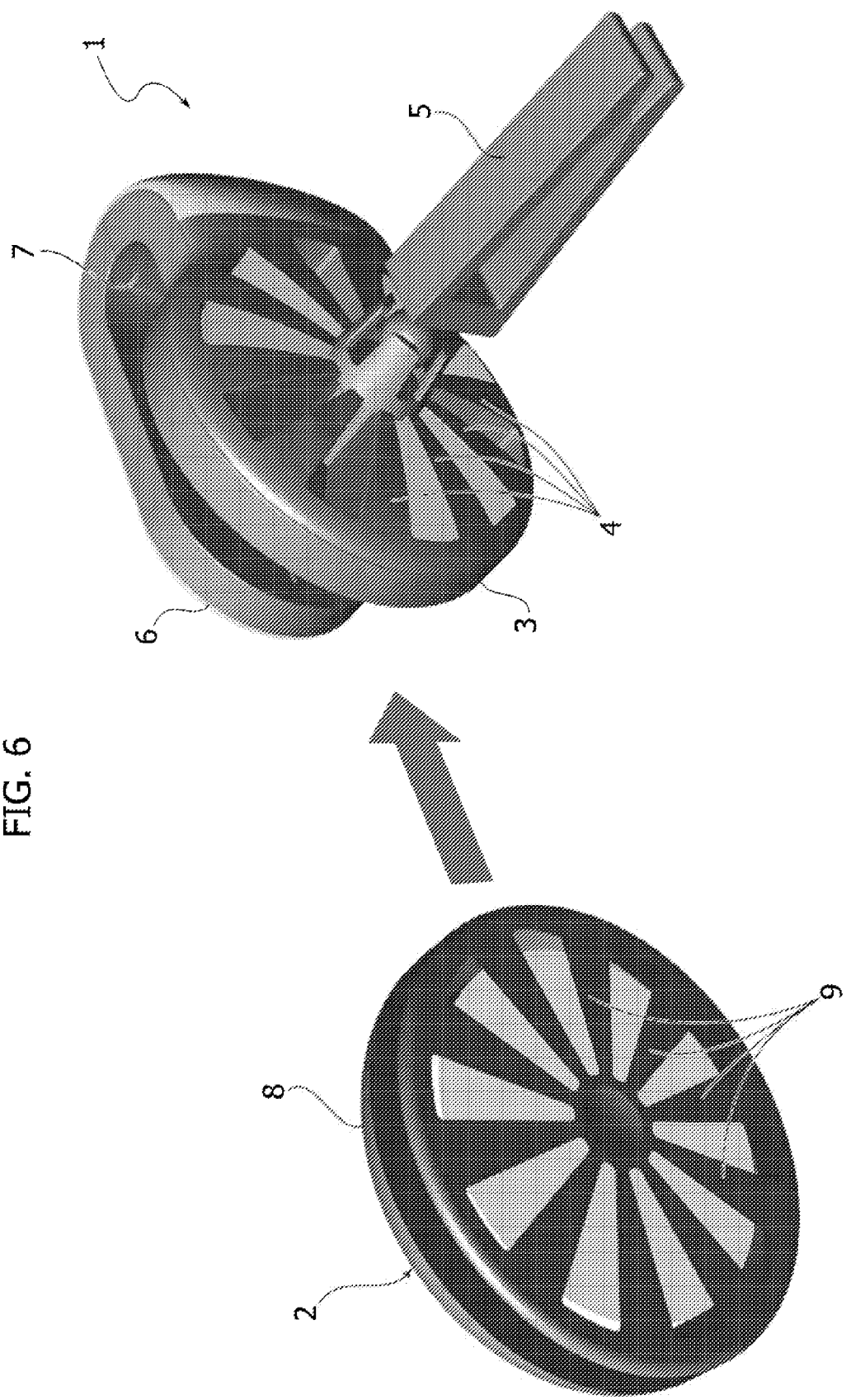

With reference to the drawings, the perfume dispenser for motor vehicles according to the invention comprises a support designated as a whole by 1, and a perfume-dispensing body 2.

The support 1 comprises a generally circular base 3 provided with a spoke-like configuration of slits 4, progressively tapered from the periphery to the centre of the base 3, and with an articulated dorsal attachment 5 for coupling to a supporting structure of a vehicle.

The support 1 further comprises a front arm 6 connected to the base 3 and bent in front of this according to a roughly J-shaped configuration so as to form an open receptacle 7.

The perfume-dispensing body 2 consists of a flattened cylindrical casing 8 set in a projecting way peripherally within the receptacle 7 and connected in a coaxially rotatable way to the base 3 of the support 1. The casing 8 has dorsal slits 9 similar to the slits 4 of the base 3 of the support 1 and facing these, and contains a hydrophilic material soaked with a perfumed fluid. This hydrophilic material is conveniently a constant-volume absorbent material.

It will emerge clearly from the foregoing that, in use, by rotating the perfume-dispensing body 2 with respect to the support 1 it is possible to vary the relative positions of the slits 9 and the slits 4 so as to increase or reduce selectively the passages of flow of the perfumed fluid towards the environment inside the motor vehicle.

Of course, the details of construction and the embodiments may vary widely with respect to what has been described and illustrated, without thereby departing from the scope of the present invention as defined in the ensuing claims. Thus, for example, the surface conformation and the material of the front arm 6 may be extremely varied, also in order to enhance the general appearance of the perfume dispenser.

The invention claimed is:

1. A perfume dispenser for motor vehicles comprising:
   a support bearing a perfume-dispensing body;
   the support comprising a generally circular base provided with slits and with an articulated dorsal attachment for coupling to a supporting structure of a motor vehicle, and a front arm connected to the base and bent in front of the base to form an open receptacle; and
   the perfume-dispensing body consisting of a flattened cylindrical casing set peripherally projecting within said receptacle and connected in a coaxially rotatable way to said base, said casing containing a hydrophilic material soaked with a perfumed fluid and having dorsal slits facing said slits of the base of the support.

2. The perfume dispenser according to claim 1, wherein said front arm is roughly shaped like a J.

3. The perfume dispenser according to claim 1, wherein said slits are arranged like spokes.

4. The perfume dispenser according to claim 3, wherein said slits arranged like spokes are tapered from a periphery to a center of said base and of said casing, respectively.

5. The perfume dispenser according to claim 1, wherein said hydrophilic material is a constant-volume absorbent material.

6. The perfume dispenser according to claim 2, wherein said slits are arranged like spokes.

7. The perfume dispenser according to claim 2, wherein said hydrophilic material is a constant-volume absorbent material.

8. The perfume dispenser according to claim 3, wherein said hydrophilic material is a constant-volume absorbent material.

9. The perfume dispenser according to claim 4, wherein said hydrophilic material is a constant-volume absorbent material.

* * * * *